United States Patent [19]

Rosini et al.

[11] Patent Number: 5,663,389

[45] Date of Patent: Sep. 2, 1997

[54] 3,4-DIHYDRO-2-IODOMETHYL-2,5,7,8-TETRAMETHYL-2H-1-BENZOPYRANS

[75] Inventors: Goffredo Rosini, Bologna; Claudia Baldazzi, Emilia; Silvano Piani, Bologna, all of Italy

[73] Assignee: Alfa Wassermann S.p.A., Alanno, Italy

[21] Appl. No.: 611,796

[22] Filed: Mar. 6, 1996

[30] Foreign Application Priority Data

Apr. 14, 1995 [IT] Italy .................. BO95A0167

[51] Int. Cl.$^6$ .................................. C07D 311/58
[52] U.S. Cl. ............................ 549/410; 549/408
[58] Field of Search ........................ 549/408, 410

[56] References Cited

U.S. PATENT DOCUMENTS 5,313,007   5/1994   Laffan .................. 568/765

Primary Examiner—Johann Richter
Assistant Examiner—Laura L. Stockton
Attorney, Agent, or Firm—Bucknam and Archer

[57] ABSTRACT

The present invention refers to compounds having a benzopyranic structure of general formula I

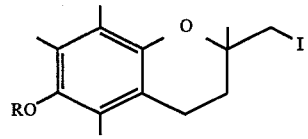

wherein R represents a hydrogen atom or an acyl group, useful as intermediates in the synthesis of vitamin E and of other compounds having benzopyranic structure endowed with properties inhibiting the formation of organic peroxides and therefore having antioxidizing activity, and to the process for their preparation.

1 Claim, No Drawings

3,4-DIHYDRO-2-IODOMETHYL-2,5,7,8-TETRAMETHYL-2H-1-BENZOPYRANS

BACKGROUND OF THE INVENTION

Vitamin E, known also as α-tocopherol, of formula

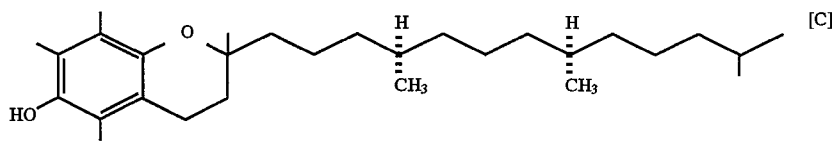

is an important nutritional factor both for humans and animals, endowed with antioxidizing activity that protects the cells from the oxidation and therefore from the degeneration. It is present in nature in vegetable oils and legumes and is produced also by chemical synthesis. The total synthesis of vitamin E, described from H. Mayer et al. in Helvetica Chimica Acta, 46, 650, (1963), is carried out by means of the Wittig's condensation between the aldehydic derivative A having chromanic structure and the phosphonium salt of an alkyl derivative having 15 carbon atoms (compound B), obtained by chemical modification of the natural compound phytol, and subsequent hydrogenation of the double bond between the positions 1' and 2' as reported in the hereinbelow Scheme 1.

J. W. Scott et al. in Helvetica Chimica Acta 59, 290–306, (1976) show an alternative synthetic, method wherein the Wittig's reaction is used for the formation of the carbon-carbon bond between positions 2'–3' instead of between positions 1'–2' as reported in the hereinbelow Scheme 2.

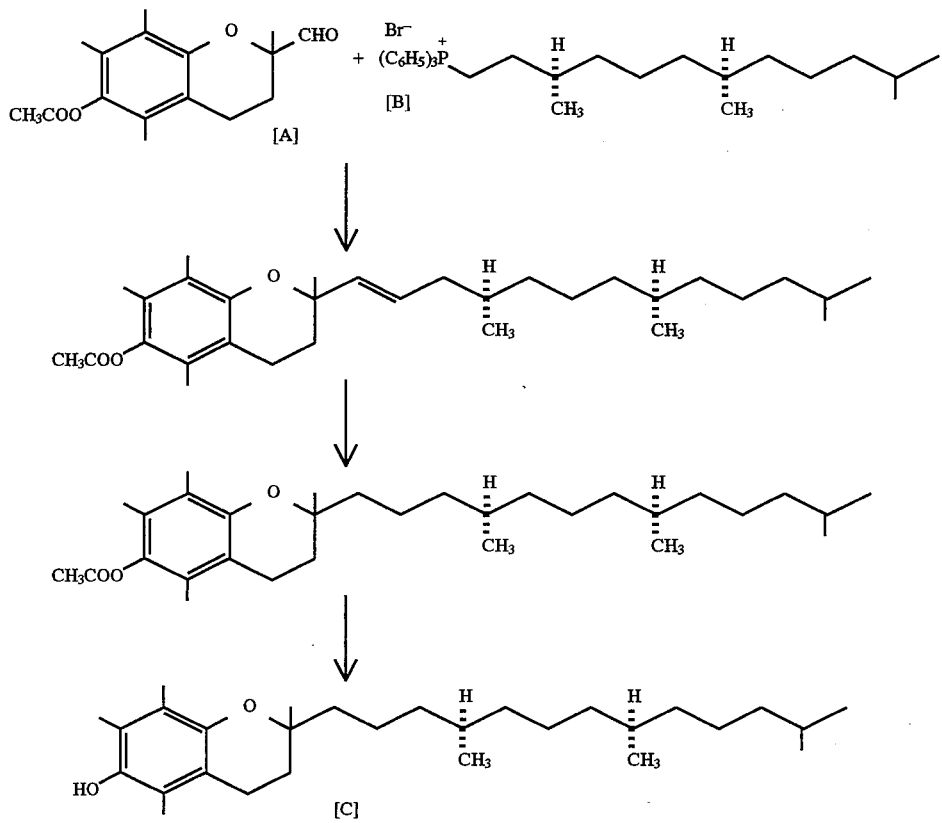

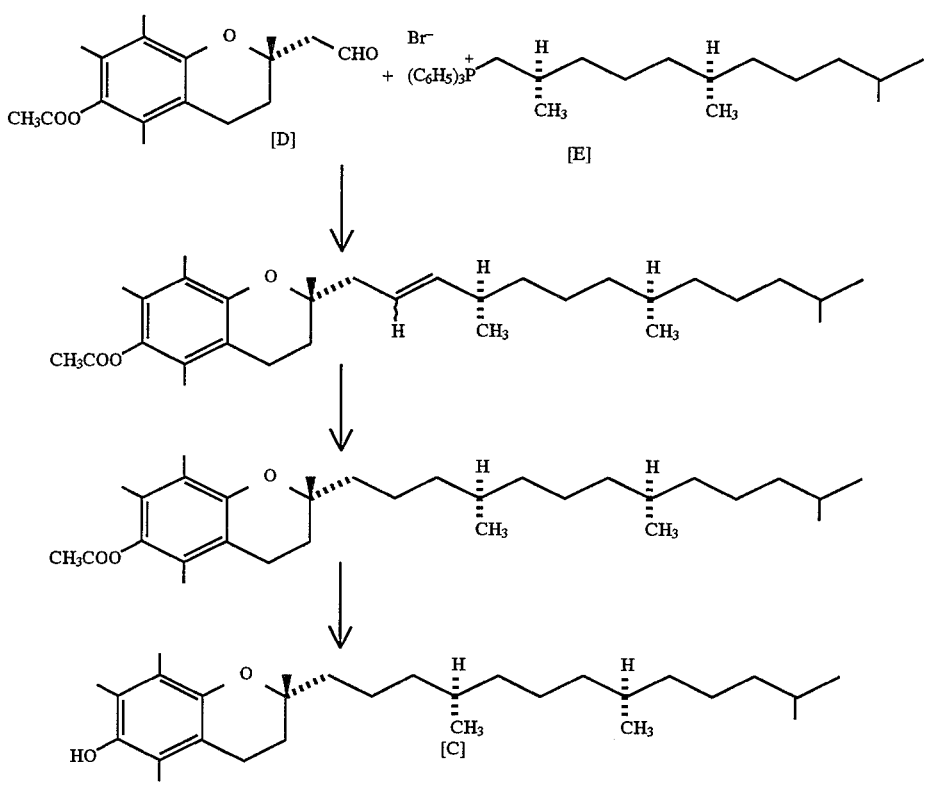
The synthesis requires the preparation of a chromanic synthon (D) superior homologue (Scheme 3) and of an alkyl residue (E) inferior homologue (Scheme 4) in respect of those described from H. Mayer et al., always through a series of reactions quite complex and little convenient both from a practical and an economical point of
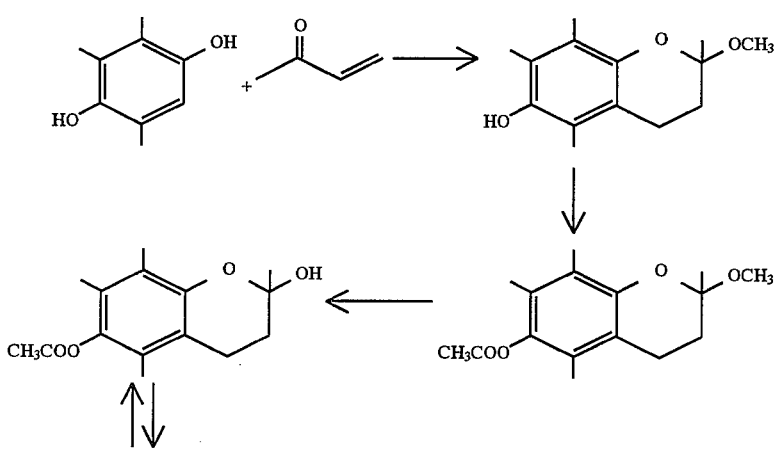

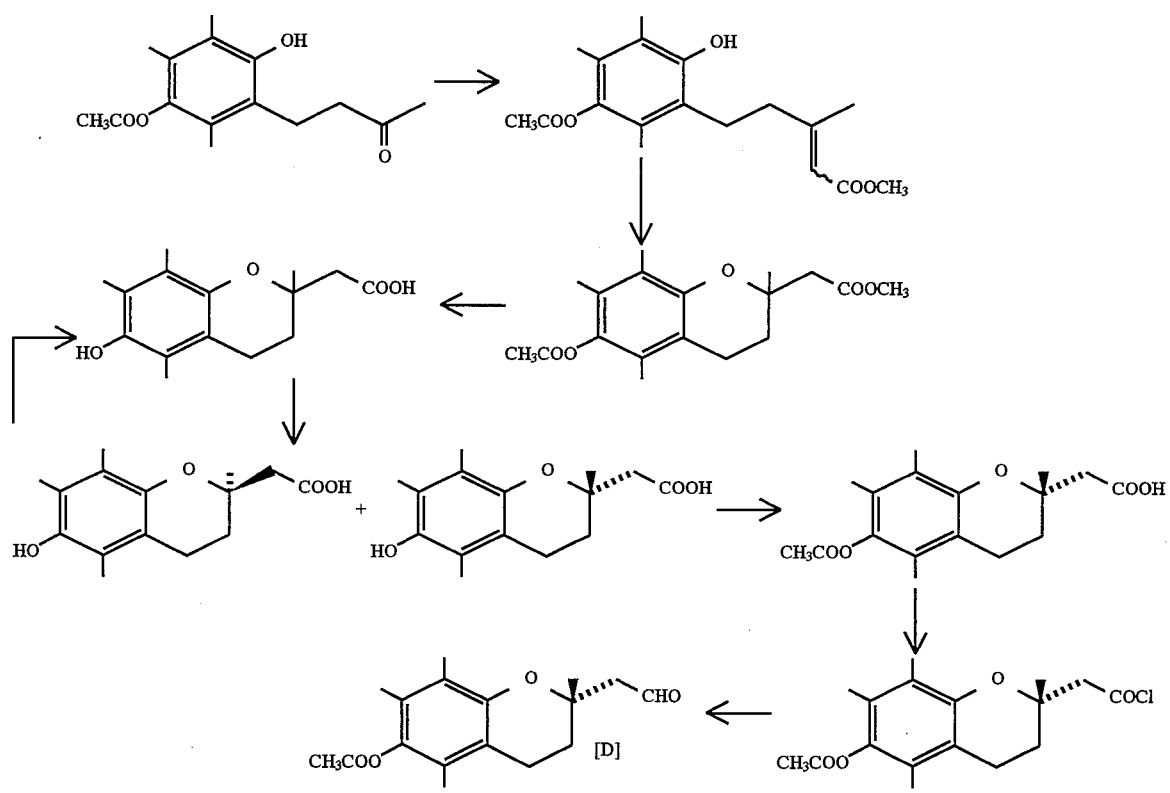
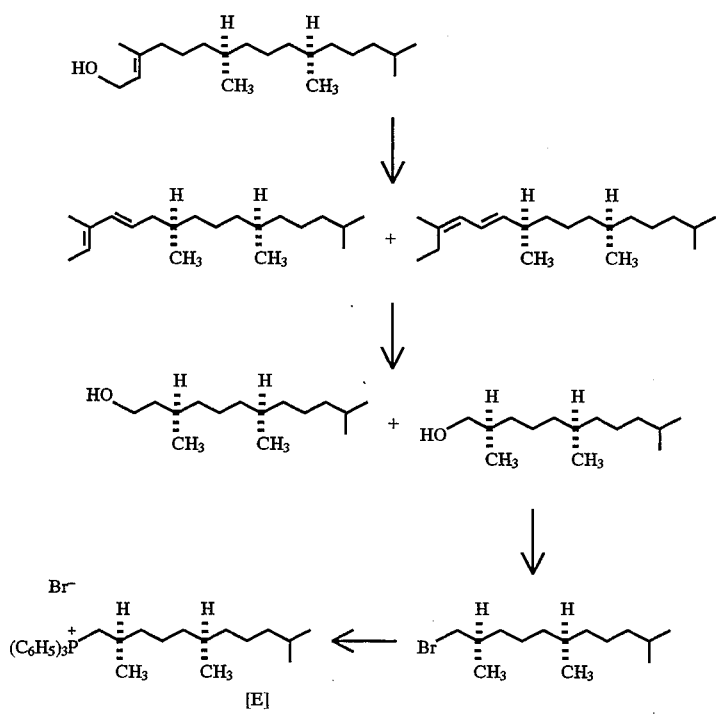

Both described methods described hereinabove provide for the introduction of a functionalization of aldehydic type on the chromanic residue that requires a high number of reactions with considerable disadvantages both from the practical point of view and in terms of yield and of a functionalization of halide type on the alkyl residue, with the aim to allow a synthetic approach by means of the Wittig's reaction, also remarkably complicated and therefore little practical and poorly profitable from an industrial point of view. An alternative synthetic strategy that better complies with criteria of practicality and economy can be drafted by considering the preparation of a functionalization of halide type on the residue with chromanic structure with the aim to arrange for the preparation of the phosphonium salt useful for the Wittig's condensation reaction. The halide derivatives on the residue with chromanic structure of formula I

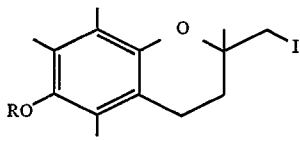

are not known and form the object of the present invention together with the process to obtain them. A further advantage of this alternative method is represented by the fact that the aliphatic chain has to be functionalized by means of an aldehydic group and that this aldehydic derivative can be obtained from the phytol by means of a series of reactions lower in respect to the series of reactions necessary to get the [B] or [E] aliphatic derivatives. A further application of the compounds of formula I is possible in the synthesis of compounds with benzopyranic structure having side chain different from that of vitamin E, but endowed with similar properties, antioxidizing and inhibiting the formation of lipid peroxides recently reported in literature, for instance from P. A. McCarthy in Med. Res. Rew. 13, 135–159, (1993). Such derivatives can easily be synthesized by utilizing the chemical reactivity of the alkylhalide functional group in side chain to the chromanic residue present in the compounds of general formula I that forms the object of the present invention. One of these products is troglitazone, also known as CS-045, which is part of a series of derivatives having benzylthiazolidinic structure of general formula

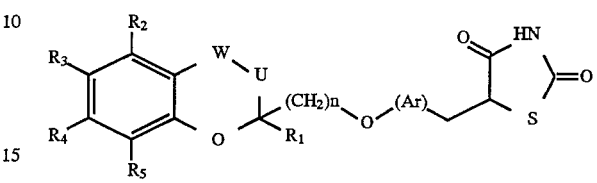

endowed with properties inhibiting the formation of lipidic peroxides, proposed in the therapy and prevention of atherosclerosis and of diabetic complications caused by processes of lipidic peroxidation and described in U.S. Pat. No. 4,873,255. The synthetic method used for the preparation of the troglitazone of formula

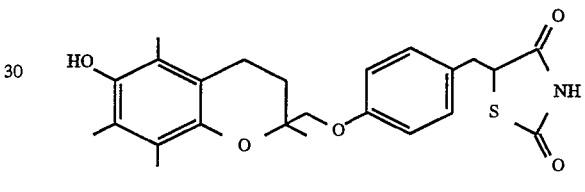

described in Drugs of the Future, 14, 847, (1989) and in U.S. Pat. No. 4,873,255 provides for two alternative routes illustrated in Schemes 5 and 6.

Scheme 5

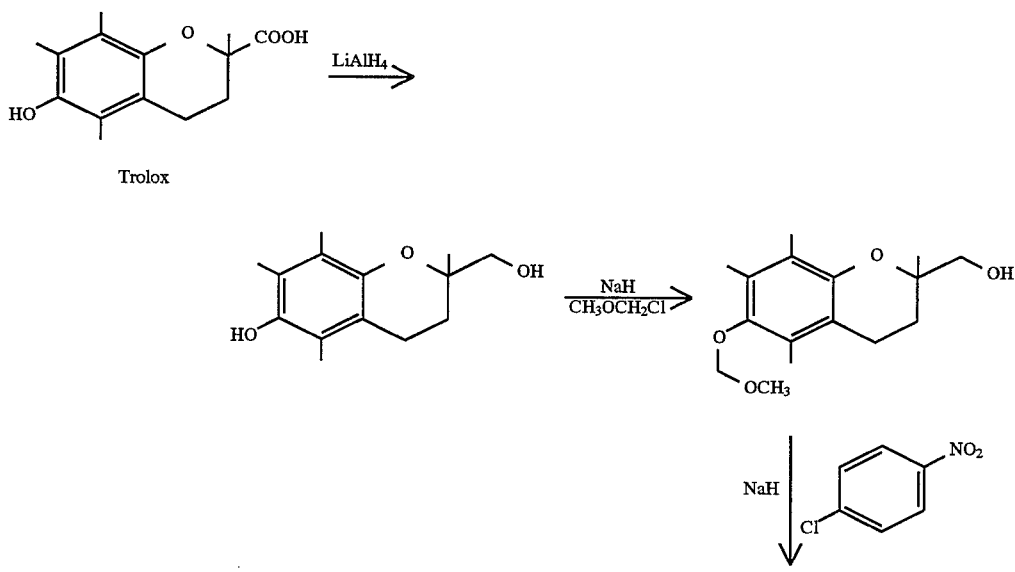

Trolox

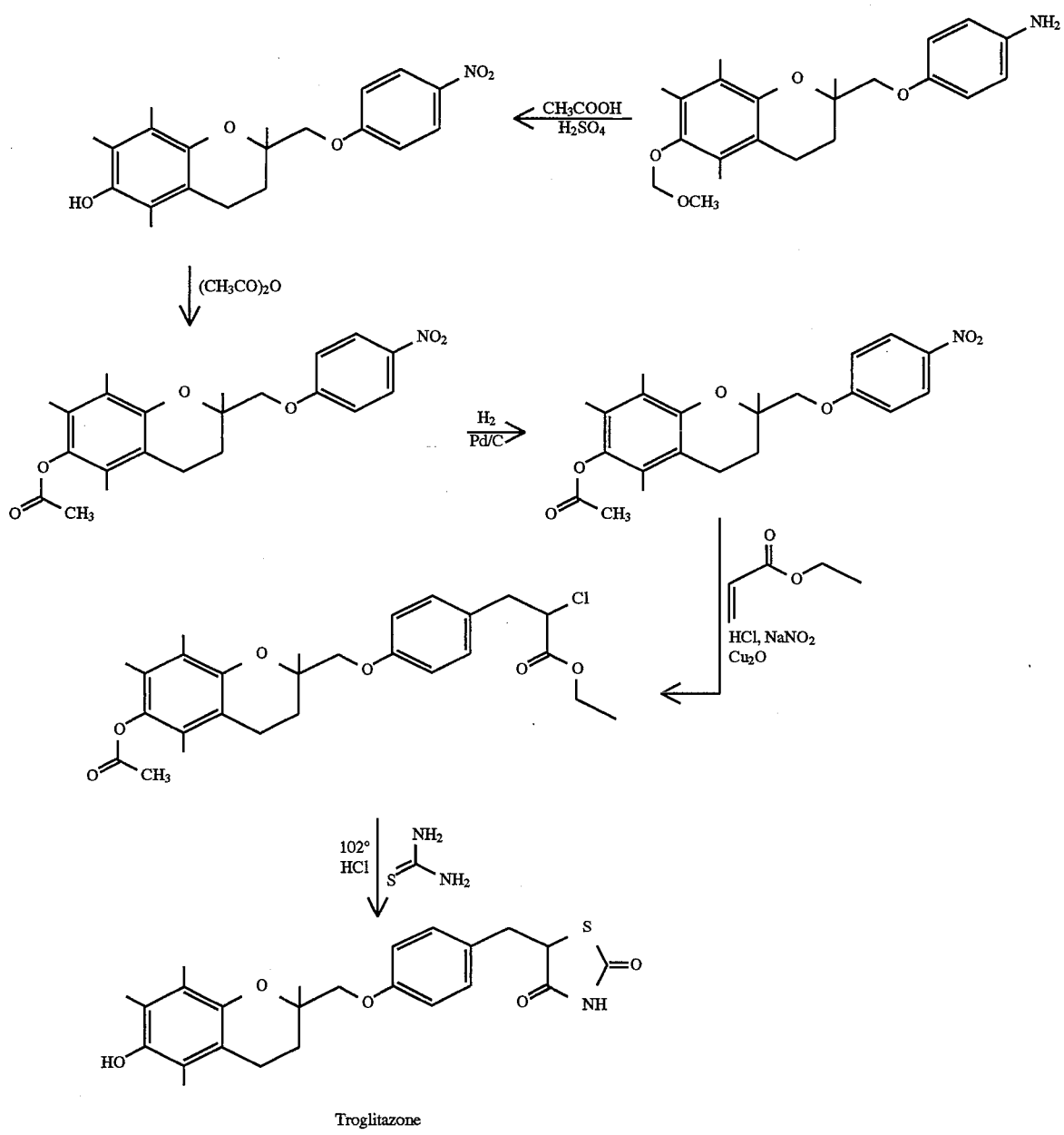
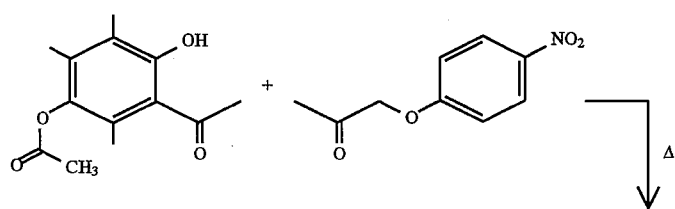
Scheme 6

-continued
Scheme 6

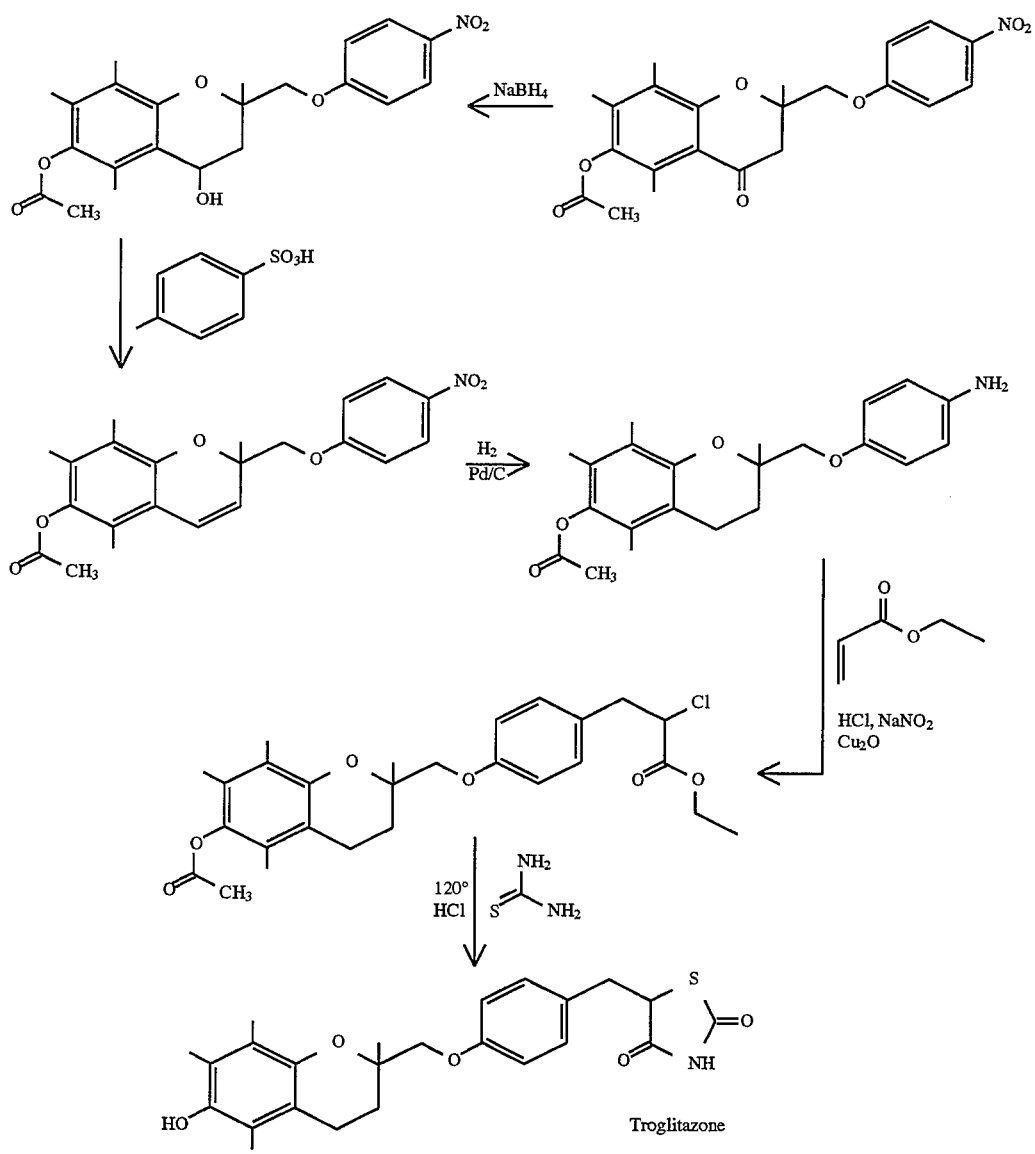

The starting material of the first route is represented by trelox, 6-hydroxy-2,5,7,8-tetramethyl-chroman-2-carboxylic acid, described in the literature and used as antioxidizer. Troglitazone, at present clinically tested as antidiabetic and antiatherosclerotic, is prepared (Scheme 5) by reduction of the carboxy group in position 2 to alcoholic group, subsequent protection of the hydroxylic group of phenolic type, condensation with 4-nitro-chlorobenzene, substitution of the protective group on the phenolic hydroxyl with the acetyl group, reduction of the nitro group, condensation with ethyl acrylate through an intermediate diazonium salt and lastly cyclization with thiourea. The alternative route (Scheme 6) instead provides starting product a suitably substituted acetophenone obtainable starting from the trimethylhydroquinone with a series of known reactions and from which by cyclization with 4-nitrophenoxyacetone the chromanic derivative substituted in position 2 is obtained which by subsequent reduction of the carbonyl in position 4, dehydration of the obtained alcohol and contemporary reduction of the double bond and of the nitro group in side chain allows to get the aminic intermediate already considered in the previous Scheme. The process described for the preparation of the compounds of general formula I object of the present invention is certainly more practical and less complicated of those previously described for the synthesis of the intermediates of the vitamin E and of the troglitazone and therefore the claimed derivatives result extremely effective intermediates for a process of industrial manufacture more advantageous of these two drugs. Moreover they can represent valid starting compounds for the synthesis of molecules analogous to vitamin E endowed with antioxidizing properties, useful in fields other than the pharmaceutical field, like in the stabilization of the plastics to the oxidizing agents or in the conservation of foodstuffs.

DESCRIPTION OF THE INVENTION

The present invention refers to compounds with bonzopyranic structure of general formula I

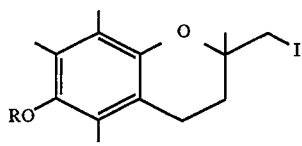

wherein R represents a hydrogen atom or an acyl group, useful as intermediates in the synthesis of vitamin E and of other compounds with benzopyranic structure endowed with properties inhibiting the formation of organic peroxides and therefore with antioxidizing activity, usable as drugs in the therapy and prevention of atherosclerosis and of diabetic complications and as antioxiders in the conservation of the foodstuffs and in the stabilization of the plastics, and to the process for their preparation.

The compounds preferred in the realization of the present invention are those where R represents a hydrogen atom, an acyl group or a benzoyl group.

The compounds of general formula I are obtained through the process reported in the hereinbelow Scheme 7.

alcohols, ethers and hydrocarbons. The butene of formula IV, wherein R is a hydrogen atom, is obtained by alkaline hydrolysis of the butene of formula III, step [b], by using for each molar equivalent of butene of formula III from 5 to 10 molar equivalents of an inorganic base selected from potassium hydroxide and sodium hydroxide dissolved in an alcohol having from 1 to 3 carbon atoms containing from 3% to 10% of water, preferably 95% ethyl alcohol, at a temperature between 20° C. and the boiling temperature of the reaction mixture for a period of time between 2 and 24 hours. The iodomethylderivatives of generale formula I are obtained by reacting, step [c], a molar equivalent of a compound of formula III or IV in an aqueous solution containing from 1 to 2 molar equivalents of a base selected from the hydroxides of the alkali or alkali-earth metals, preferably sodium hydroxide, with a solution containing a strong excess of potassium or sodium iodide, from 8 to 15 molar equivalents, and of iodine, from 2 to 5 molar equivalents, in a polar solvent selected from water and alcohols containing from 1 to 3 carbon atoms, preferably water, at a temperature comprised between 10° C. and 50°

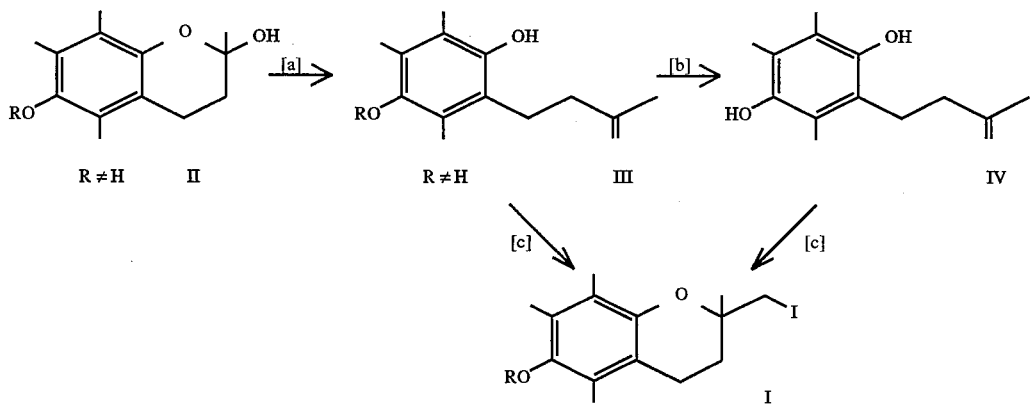

Scheme 7

The starting dihydrobenzopyran of general formula II wherein R is different from hydrogen is obtained by the trimethylhydroquinone by using methods similar to those described by J. W. Scott et al. in Helvetica Chimica Acta, 59, 290–306, (1976). It is submitted to a Wittig reaction, step [a], with methyltriphenylphosphonium bromide in presence of sodium hydride in order to obtain the butene of formula III wherein R is different from hydrogen. From 3 to 5 molar equivalents of sodium hydride, dissolved in dimethylsulphoxide, are heated to 60° C. for 30 minutes and then are reacted with a solution containing from 2 to 4 molar equivalents of methyltriphenylphosphonium bromide in dimethylsulphoxide for a period of time between 30 minutes and one hour at a temperature between 10° C. and 25° C. under nitrogen atmosphere and under strong stirring. A molar equivalent of a dihydrobenzopyran of general formula II dissolved in an organic solvent, preferably anhydrous tetrahydrofuran, is added to this reaction mixture, and the reaction mixture is kept at a temperature between 50° C. and 70° C. for a period of time between 30 minutes and one hour. The compound, obtained by evaporating the solvent, is purified by filtration on silica gel by using as eluent an organic solvent preferably selected between ethers and hydrocarbons or mixtures thereof. The solid obtained by evaporation of the elution solvent is then crystallized from a solvent or a mixture of organic solvents selected from C. for a period of time comprised between 16 and 24 hours. The crude product obtained by evaporating the solvent is first purified by chromatography on a column of silica gel by using as eluents solvents selected from ethers or straight chain or cyclic hydrocarbons or mixtures thereof and then the solid obtained by evaporating the elution solvent is crystallized from ethers or straight chain or cyclic hydrocarbons or organic chlorinated solvents or mixtures thereof. The determination of the melting point has been carried out by means of an Electrothermal capillary melting point instrument, without any correction. The I.R. spectrum has been obtained by means of model 983/G Perkin-Elmer spectrophotometer generally, when not otherwise specified, by preparing the specimen in KBr and by recording the spectrum between 4000 and 600 nm. The $^1$H-NMR spectrum has been recorded at room temperature by means of a Varian Gemini spectrometer at 200 MHz, by using tetramethylsilane as internal standard and deuterochloroform as solvent; the resonances of the signals have been expressed as p.p.m. The $^{13}$C-NMR has been carried out at 50.3 MHz with a Varian Gemini 200 spectrometer by using tetramethyisilane as internal standard and deuterochloroform as solvent. The mass spectrum has been recorded by using a VG 7070E mass spectrometer, at an ionization voltage of 70 eV and at an acceleration voltage of 6 Kvolt. The chromatographies on silica gel have been carried out by using silica gel 60 F254

(230–400 mesh-Merck) with the eluents reported in the examples, according to the technique described by W. Clark Still et al. in J. Org. Chem., 43, 2923, (1978). The examples hereinbelow reported have to be considered as an illustration of the present invention and not as an its limitation.

EXAMPLE 1

6-Acetoxy-3,4-dihydro-2-iodomethyl-2,6,7,8-tetramethyl-2H-1-benzopyran a) 4-(5-Acetoxy-2-hydroxy-3,4,6-trimethylphenyl)-2-methyl-1-butene A solution containing 1.13 g (0.046 moles) of sodium hyddde in 21 ml of dimethylsulphoxide is heated at the temperature of 60° C. for 30 minutes, then is cooled to the temperature of 15° C. and, under nitrogen atmosphere, a solution containing 12.18 g (0.034 moles) of methyltriphenylphosphonium bromide in 36 ml of dimethylsulphoxide is slowly added. The reaction mixture is kept under strong stirring for 40 minutes at room temperature and then is quickly added to a solution containing 3.0 g (0.0114 moles) of 6-acetoxy-3,4-dihydro-2-hydroxy-2,5,7,8-tetramethyl-2H-1-benzopyran in 9 ml of anhydrous tetrahydrofuran and heated at a temperature of 60° C. for 45 minutes. The product is extracted with ethyl ether from the reaction mixture, recovered by evaporating the solvent, purified by filtration on a layer of silica gel 5 cm high, by eluting with an ethyl ether—petroleum ether mixture in 1:1 ratio and recovered by subsequent evaporation of the elution solvent. The pure product, 2.12 g with a yield of 71%, is obtained by crystallization from ethyl ether and n-hexane and shows the following chimico; physical characteristics: m.p.=122°–123° C.

$^1$H-NMR (CDCl$_3$) δ (ppm): 1.78 (s, 3H, CH$_2$=CCH$_3$); 1.95–2.2 (m, 11H, 3 arom. CH$_3$ and CH$_2$C=CH$_2$); 2.35 (s, 3H, CH3CO); 2.6–2.75 (m, 2H, CH$_2$CH$_2$C=CH$_2$); 4.75 (s, 2H, CH$_2$=C); 4.9 (s, 1H, OH).

$^{13}$C-NMR (CDCl$_3$) δ (ppm): 12.61 (arom. CH$_3$); 12.86 (arom. CH$_3$); 13.58 (arom. CH$_3$); 21.02 (CH$_3$); 23.15 (CH$_3$); 26.33 (CH$_2$); 37.52 (CH$_2$); 110.46 (CH$_2$); 121.23; 125.69; 126.33; 127.00; 142.11 (5 arom. C); 146.65 (ethylenic Cq); 150.03 (arom. C); 170.44 (CO).

IR (KBr), ν (cm$^{-1}$): 3468 (OH), 1742 (CO).

MS (m/z):262 (M$^+$); 245, 220, 164.

b) 6-Acetoxy-3,4-dihydro-2-iodomethyl-2,6,7,8-tetramethyl-2H-1-benzopyran 1.5 Grams (0.0057 moles) of 4-(5-acetoxy-2-hydroxy-3,4,6-trimethylphenyl)-2-methyl-1-butane are dissolved in a solution containing 0.24 g (0.006 moles) of sodium hydride in 15.6 ml of water at the temperature of 10° C. The mixture is kept under stirring for 20 minutes and then is slowly added with a solution containing 10.44 g (0.063 moles) of potassium iodide and 5.1 g (0.0201 moles) of iodine in 10.2 ml of water. The reaction mixture is kept at room temperature for 5 hours and at 40° C. for 17 hours and then is diluted with methylene chloride and added with sodium sulphite till decoloration. The organic layer containing the product is separated and the crude product obtained by evaporation of the solvent is purified by chromatography on a column of silica gel with eluent ethyl ether and petroleum ether in 1:4 ratio. After evaporating the elution solvent the pure product, 1.23 g with yield of 55%, is obtained by crystallization from ethyl ether and n-hexane. It shows the following chimico-physical characteristics: m.p.=74°–76° C.

$^1$H-NMR (CDCl$_3$) δ (ppm): 1.4 (s, 3H, CH$_3$); 1.75–2.2 (m, 11H, 3 arom. CH$_3$ and OCCH$_2$); 2.35 (s, 3H, CH$_3$CO); 2.55–2.65 (t, J=7.7 Hz, 2H, CH$_2$CH$_2$CO); 3.35 (s, 2H, CH$_2$I).

$^{13}$C-NMR (CDCl$_3$) δ (ppm): 12.03 (arom. CH$_3$); 12.24 (arom. CH$_3$); 13.04 (arom. CH$_3$); 15.10 (CH$_2$); 20.65 (CH$_2$ and CH$_3$); 25.46 (CH$_3$); 30.32 (CH$_2$); 73.49 (Cq); 117.39; 123.87; 125.54; 127.73; 141.82; 149.25 (6 arom. C); 169.99 (CO).

IR (KBr), ν (cm$^{-1}$): 3502 (OH), 1750 (CO).

MS (m/z): 388 (M+); 346, 219, 191,165.

EXAMPLE 2

3,4-Dihydro-6-hydroxy-2-iodomethyl-2,5,7,8-tetramethyl-2H-1-benzopyran a) 4-(2,5-Dihydroxy-3,4,6-trimethylphenyl)-2-methyl-1-butene A solution containing 7.6 g (0.029 moles) of 4-(5-acetoxy-2-hydroxy-3,4,6-trimethylphenyl)-2-methyl-1-butene in 90 ml of 95% ethyl alcohol, is added with 90 ml of a solution containing 14.9 g (0.264 moles) of potassium hydroxide in 95% ethyl alcohol. The reaction mixture is kept for 22 hours at 90° C., then is diluted by adding ethyl ether and water, acidified to pH 5 with a 10% aqueous solution of hydrochloric acid and the product is extracted with ethyl ether. The crude product is obtained by evaporation of the solvent and used without further purification.

b) 3,4-Dihydro-6-hydroxy-2-iodomethyl-2,6,7,8-tetramethyl-2H-1-benzopyran

In a solution containing 0.92 g (0.023 moles) of sodium hydroxide in 37 ml of water 2.53 g (0.0115 moles) of 4-(2,5-dihydroxy-3,4,6-trimethylphenyl)-2-methyl-1-butene are dissolved at the temperature of 13° C. and then a solution containing 21.0 g (0.126 moles) of potassium iodide and 10.2 g (0.04 moles) of iodine in 20 ml of water is slowly added. The reaction mixture is kept at room temperature for 24 hours and then is diluted with methylene chloride and added with sodium sulphite till decoloration of the solution from the dark violet to the yellow colour. The organic layer containing the product is separated and the crude product obtained through evaporation of the solvent is purified by chromatography on a column of silica gel with eluent ethyl ether and petroleum ether in 2:3 ratio. After evaporating the elution solvent, the pure product, 1.4 g with 3.5% yield, is obtained by crystallization from an ethyl ether and n-hexane mixture. It shows the following chimico-physical characteristics: m.p.=109°–111 ° C.

$^1$H-NMR (CDCl$_3$) δ (ppm): 1.4 (s, 3H, CH$_3$); 1.7–2.2 (m, 11H, 3 arom. CH$_3$ and OCCH$_2$); 2.55–2.7 (t, J=7.7 Hz, 2H, CH$_2$CH$_2$C); 3.3 (s, 2H, CH$_{2I}$); 4,3 (s, 1H, OH).

$^{13}$C-NMR (CDCl$_3$) δ (ppm): 11.51 (arom. CH$_3$); 12.05 (arom. CH$_3$); 12.40 (arom. CH$_3$); 15.30 (CH$_2$); 20.83 (CH$_2$); 25.49 (CH$_3$); 30.59 (CH$_2$); 73.00 (Cq); 117.32 119.03; 121.94; 123.46; 145.40; 145.74 (6 arom. C).

IR (KBr), ν (cm$^{-1}$): 3502 (OH).

MS (m/z):346 (M$^+$); 219; 191; 165.

We claim:

1. The compound 6-acetoxy-3,4-dihydro-2-iodomethyl-2,5,7,8,-tetramethyl-2H-1-benzopyran of formula

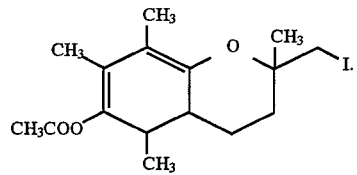

* * * * *

UNITED STATES PATENT AND TRADEMARK OFFICE
CERTIFICATE OF CORRECTION

PATENT NO. : 5,663,389        Page 1 of 2
DATED     : September 2, 1997
INVENTOR(S) : GOFFREDO ROSINI, CLAUDIA BALDAZZI, SILVANO PIANI It is certified that error appears in the above-identified patent and that said Letters Patent is hereby corrected as shown below:

Please correct the chemical formulae in Column 10 of the patent as follows:

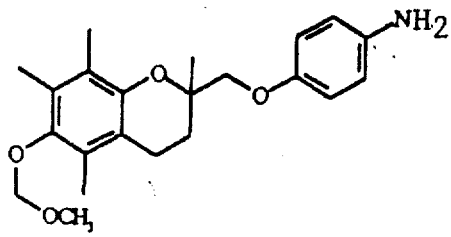

From:

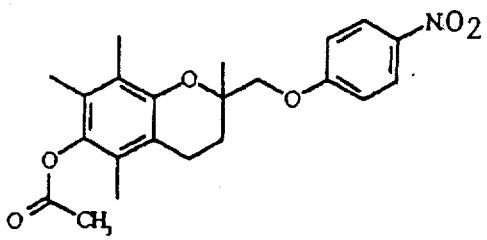

-------------------------------------------------

UNITED STATES PATENT AND TRADEMARK OFFICE
CERTIFICATE OF CORRECTION

PATENT NO. : 5,663,389
DATED : September 2, 1997
INVENTOR(S) : GOFFREDO ROSINI, CLAUDIA BALDAZZI, SILVANO PIANI It is certified that error appears in the above-identified patent and that said Letters Patent is hereby corrected as shown below:

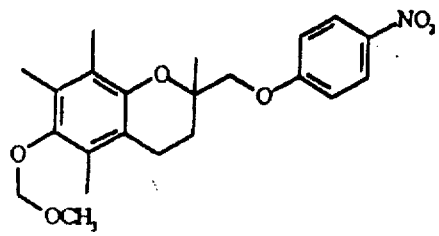

To:

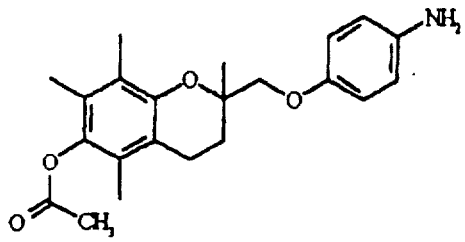

Signed and Sealed this

Ninth Day of December, 1997

*Attest:*

BRUCE LEHMAN

*Attesting Officer*     *Commissioner of Patents and Trademarks*